(12) United States Patent
Schachar

(10) Patent No.: US 8,771,349 B2
(45) Date of Patent: Jul. 8, 2014

(54) APPARATUS AND METHOD FOR PREVENTING GLAUCOMATOUS OPTIC NEUROPATHY

(76) Inventor: Ira Hyman Schachar, Dallas, TX (US)

( * ) Notice: Subject to any disclaimer, the term of this patent is extended or adjusted under 35 U.S.C. 154(b) by 1385 days.

(21) Appl. No.: 12/033,478

(22) Filed: Feb. 19, 2008

(65) Prior Publication Data

US 2009/0210053 A1   Aug. 20, 2009

(51) Int. Cl.
*A61F 2/14* (2006.01)
*A61F 9/007* (2006.01)
*A61N 1/36* (2006.01)

(52) U.S. Cl.
CPC ......... *A61F 9/00781* (2013.01); *A61F 9/00727* (2013.01); *A61N 1/36046* (2013.01)
USPC .............. 623/6.63; 606/152; 607/53; 607/54; 607/154

(58) Field of Classification Search
USPC .......... 623/4.1, 6.63, 6.64; 514/954; 606/107, 606/152; 607/154, 53, 54
See application file for complete search history.

(56) References Cited

U.S. PATENT DOCUMENTS

| 5,935,155 | A  | * | 8/1999  | Humayun et al. ............. 607/54 |
| 6,059,828 | A  | * | 5/2000  | Peyman ....................... 623/4.1 |
| 6,886,565 | B2 | * | 5/2005  | Morris et al. ................ 128/846 |
| 2004/0254517 | A1 | * | 12/2004 | Quiroz-Mercado et al. ...... 604/8 |
| 2006/0058857 | A1 | * | 3/2006  | Tano et al. ..................... 607/54 |
| 2006/0224212 | A1 | * | 10/2006 | Kennedy ........................ 607/54 |
| 2006/0258994 | A1 | * | 11/2006 | Avery ........................... 604/294 |
| 2007/0191910 | A1 | * | 8/2007  | Ren ................................ 607/54 |
| 2008/0183242 | A1 | * | 7/2008  | Tano et al. ..................... 607/53 |
| 2009/0287275 | A1 | * | 11/2009 | Suaning et al. ................. 607/54 |

FOREIGN PATENT DOCUMENTS

RU         2235529 C1 * 9/2004

* cited by examiner

*Primary Examiner* — David H Willse
*Assistant Examiner* — Javier Blanco
(74) *Attorney, Agent, or Firm* — Carlos R. Villamar; The Villamar Firm PLLC

(57) ABSTRACT

A device and method is disclosed for preventing glaucomatous optic neuropathy, an affliction of the eye. An incision is made in the scleral region of the eye and an optic nerve head shield is inserted and positioned proximate to the optic nerve head of the eye to form a pressure seal over the optic nerve head of the eye. The optic nerve head shield decreases the pressure differential across the cribiform plate preventing bowing of the cribiform plate and glaucomatous optic neuropathy.

8 Claims, 5 Drawing Sheets

APPARATUS AND METHOD FOR PREVENTING GLAUCOMATOUS OPTIC NEUROPATHY

The present invention relates generally to a device and method for preventing optic nerve damage from glaucoma, ocular hypertension and normal tension glaucoma by preventing bowing of the cribiform plate.

BACKGROUND OF THE INVENTION

The axons of the retinal ganglion cells pass through the cribiform plate of the eye to form the optic nerve. Changes in pressure across the cribiform plate cause the cribiform plate to bow. As a consequence of the altered shape of the cribiform plate, optic nerve fibers are damaged and this results in glaucoma which is relatively common and is manifested by cupping of the optic nerve head, visual field defects, and blindness.

Cribiform Plate

The opening in the posterior sclera, where the retinal ganglion axons exit the eye to form the optic nerve, is called the optic nerve canal. The cribiform plate is a mesh like structure extending across the optic nerve canal and is formed from the collagen and elastic fibers of the inner two thirds of the sclera. The retinal ganglion axons pass through the cribiform plate to form the optic nerve. Generally, the cribiform plate is bowed out from the eye. With increased intraocular pressure bowing of the cribiform plate increases, causing damage to the axons as they pass through the mesh of the cribiform plate. Any increase in the differential pressure across the cribiform plate will alter the shape of the cribiform plate, which can cause damage to optic nerve fibers; i.e., glaucomatous optic neuropathy.

Optic Nerve Head

The optic nerve head is formed by retinal ganglion axons as they exit the eye through the cribiform plate to form the optic nerve. Generally the retinal ganglion axons are unmyelinated and only become myelinated once they pass through the cribiform plate to form the optic nerve fibers. There are approximately 1.2 million retinal ganglion axons. The retinal ganglion axons from the macular area run almost horizontally to the optic nerve head, while those from the surrounding areas follow an arcuate pattern. The center of the optic nerve head contains the central retinal arteries and veins. The central edge of the retinal ganglion axons in the optic nerve head that surround the central arteries and veins forms the optic nerve cup. As a consequence of increased intraocular pressure, or a reduction of the perfusion pressure of the capillary supply to the optic nerve fibers, the cribiform plate bows casing damage to the optic nerve fibers at and distal to the cribiform plate. Importantly, damage to the optic nerve fibers distal to the cribiform plate occurs before any damage to the retinal ganaglion axons. With time, the retinal ganglion axons proximal to the cribiform plate eventually die causing the optic cup to enlarge, generally more vertically than horizontally, and the central blood vessels shift toward the outer edge of the optic nerve head. This enlargement of the cup of the optic nerve head is sine qua non for glaucoma. Opthalmoloscopy and fundus photography are generally used to assess the size of the optic nerve cup.

Visual Field

The visual field is defined as the extent of the physical space visible with each eye. The average visual field of each eye, when viewing straight ahead, is approximately 95° temporally, 60° nasally, 65° superiorly and 60° inferiorly. All normal eyes have a blind spot in the temporal visual field. The nasal edge of the blind spot is located approximately 15° temporal to the point of central fixation. The normal blind spot is oval with its major axis extending vertically for approximately 7° and it minor axis extending horizontally for approximately 5°. The center of the blind spot is located approximately 1.5° below the horizontal line of sight. The blind spot is the visual representation of the optic nerve head. Enlargement of the blind spot may be an early sign of retinal ganglion axonal death.

Perimetry

Perimeters are used to measure the extent of a patient's visual field. Perimeters generally use the location of the blind spot to insure proper fixation. Present perimeters rely on the subjective response of the patient's detection of a flashing light, or a moving target or a flickering sinusoidal grating to measure the visual field. The target can be different sizes and/or different colors. The light intensity and/or color of either the background and/or the target is altered to subjectively measure the threshold of the response in different areas of the visual field. There are manual perimeters, which require the operator to record the patient's response, and there are automatic perimeters, which automatically record the patient's response. The automatic perimeters have sophisticated computer algorithms to reduce the time of recording the patient' response and to improve the accuracy of the record. However, all perimeters have the disadvantage of depending on the subjective response of the patient.

Glaucoma Detection

One of the major uses of the perimeter is to detect glaucoma. Glaucoma generally occurs as a consequence of elevated intraocular pressure. The increase in intraocular pressure causes retinal ganglion axonal death in a unique pattern, which is manifested by an enlargement of the cup of the optic nerve and a visual filed defect consisting of an arcuate scotoma. The arcuate scotoma corresponds to the arcuate pattern of the damaged retinal ganglion axons. With continued elevated intraocular pressure, more of the retinal ganglion cells die and the visual field becomes reduced to just a small central area which eventually is lost and the patient becomes completely blind. Early detection of retinal ganglion axonal loss is paramount to preventing visual loss and blindness. It has been demonstrated that cupping of the optic nerve occurs before the manifestation of visual field defects. Measurements of the thickness of the retinal ganglion axon layer at and near the optic nerve further demonstrate that retinal ganglion axons may be destroyed before perimetric evidence of their death.

Measurement of Retinal Ganglion Axonal Death

There are numerous methods for detecting retinal ganglion axonal death. These methods either involve measuring the relationship of the size of the cup of the optic nerve to the size of the head of the optic nerve, and/or the thickness of the retinal ganglion axonal layer at or near the optic nerve head. These measuring methods include fundus photography, polarimetry, and optical coherent tomography. The disadvantage of these methods is they can only detect loss of retinal cell axons; i.e., after they have died.

Glaucoma Prevention and Treatment

In order to prevent the deleterious effects of glaucomatous optic neuropathy, intraocular pressure is lowered either medically and or surgically; however, even with therapy many patients go blind.

Consequently, there is a need in the art for a device that can prevent glaucomatous optic neuropathy.

SUMMARY OF THE INVENTION

The present invention disclosed herein comprises an apparatus and method for preventing glaucomatous optic neuropathy by negating the effects of intraocular pressure on the shape of the cribiform plate.

The present invention is directed to a technique for using an intraocular device implanted in the vitreous humor of the eye proximate to the optic nerve head to alter the pressure differential across the cribiform plate. In one embodiment of the invention, a biocompatible silicon shield is placed over the optic nerve head. In one aspect, the optic nerve head shield has two parts a central and a concentric peripheral part. The central part of the optic nerve shield may be convex-concave with the concave surface facing the optic nerve head. The central part of the optic nerve head shield may have a diameter comparable to the diameter of the optic nerve head. The peripheral part of the optic nerve shield may be thinner and more flexible than its central part and the peripheral part may extend beyond the edge of the optic nerve head. The peripheral part of the optic nerve shield may be in contact with the retina to provide a suction-seal between the retina and the optic nerve head shield. Once in place, the optic nerve head shield prevents intraocular pressure from altering the shape of the cribiform plate.

In another aspect, the present invention is a method for preventing glaucomatous neuropathy, including the steps of making an incision in the scleral portion of the eye, inserting the optic nerve head shield, positioning the optic nerve head shield proximate to the optic nerve head of the eye, and closing the incision. The method of the present invention may also include the steps of preparing a site within the vitreous humor for placement of the optic nerve head shield, and of using a retaining means to hold the optic nerve head shield in place.

Accordingly, it is the object of the present invention to provide prevention of glaucomatous optic neuropathy by using an optic nerve shield positioned over the optic nerve head of the eye.

It is a further object of the present invention that the optic nerve head shield prevents the effects of intraocular pressure on the cribiform plate.

It is a further object of the present invention that the optic nerve head shield prevents intraocular pressure from bowing the cribiform plate.

It is a further object of the present invention that the optic nerve head shield is held in place over the optic nerve head by suction.

It is a further object of the present invention that the optic nerve head shield is held in place over the optic nerve head by suction to the rim of the optic nerve head.

It is a further object of the present invention that the optic nerve head shield is held in place over the optic nerve by suction between the peripheral part of the optic nerve head shield and the retina concentric to the optic nerve head.

It is a further object of the present invention that the optic nerve head shield is held in place by a central peg that fits into the cup of optic nerve head of the eye.

It is a further object of the present invention that the optic nerve head shield is held in place by biocompatible hooks, pins or retinal tacks.

It is a further object of the present invention that the optic nerve head shield compartmentalizes the optic nerve head of the eye from the vitreous.

It is a further object of the present invention that the optic nerve head shield reduces the differential pressure across the cribiform plate.

It is a further object of the present invention that the optic nerve head shield is made of a biocompatible material.

It is a further object of the present invention that the optic nerve head shield is made of two or more biocompatible materials.

It is a further object of the present invention that the optic nerve head shield has a central stiff part with a flexible concentric peripheral part.

It is a further object of the present invention that the optic nerve head shield is transparent.

It is a further object of the present invention the optic nerve head shield is colored.

It is a further object of the present invention that the optic nerve head shield is opaque.

It is a further object of the present invention that the optic nerve head shield prevents the transduction of intraocular pressure to the optic nerve head.

It is a further object of the present invention that the optic nerve head shield forms a pressure seal around the optic nerve head.

It is a further object of the present invention that the optic nerve head shield forms a pressure seal with the surface of the retina.

Additional objects of the present invention will become apparent from the description of the invention that follows.

The foregoing has outlined rather broadly the features and technical advantages of the present invention so that those skilled in the art may better understand the Detailed Description of the invention that follows. Additional features and advantages of the invention will be described hereinafter that form the subject matter of the claims of the invention. Those skilled in the art should appreciate that they may readily use the conception and the specific embodiment disclosed as a basis for modifying or designing other structures for carrying out the same purposes of the present invention. Those skilled in the art should also realize that such equivalent constructions do not depart from the spirit and scope of the invention in its broadest form.

Before undertaking the Detailed Description of the Invention, it may be advantageous to set forth the definition of certain words and phrases used throughout this patent document. The terms "include" and "comprise" and derivatives thereof, mean inclusion without limitation; the term "or' is inclusive, meaning "and/or"; the phrases "associated with" and associated therewith" as well as derivatives thereof, may mean to include, be included within, interconnect with, contain, be contained within, connect to or with, couple to or with, be communicable with, cooperate with, interleave, juxtapose, to bound to or with, have, have a property of, or the like; and the term "controller," "processor," or "apparatus" means any device, system or part thereof that controls at least one operation. Such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document. Those of ordinary skill should understand that in many instances (if not in most instances), such definitions apply to prior uses, as well as to future uses, of such defined words or phrases.

BRIEF DESCRIPTION OF THE DRAWINGS

For a more complete understanding of the present invention and its advantages, reference is now made to the following description taken in conjunction with the accompanying drawings, in which like reference numerals represent like parts.

DETAILED DESCRIPTION OF THE INVENTION

FIGS. 1-5 and the various embodiments used to describe the principles of the present invention are by of illustration and should not be construed in any to limit the scope of the invention. Those skilled in the art will understand that the principles of the present invention may be implemented in any type of suitably arranged optic nerve head shield that is implanted proximate to the optic nerve head of the eye. Note that as used herein, "proximate to the optic nerve head" refers to a location in the vitreous humor, close to the optic nerve head. In some applications the optic nerve head shield will touch the optic nerve head of the eye, though this contact is not required.

Figure 1:
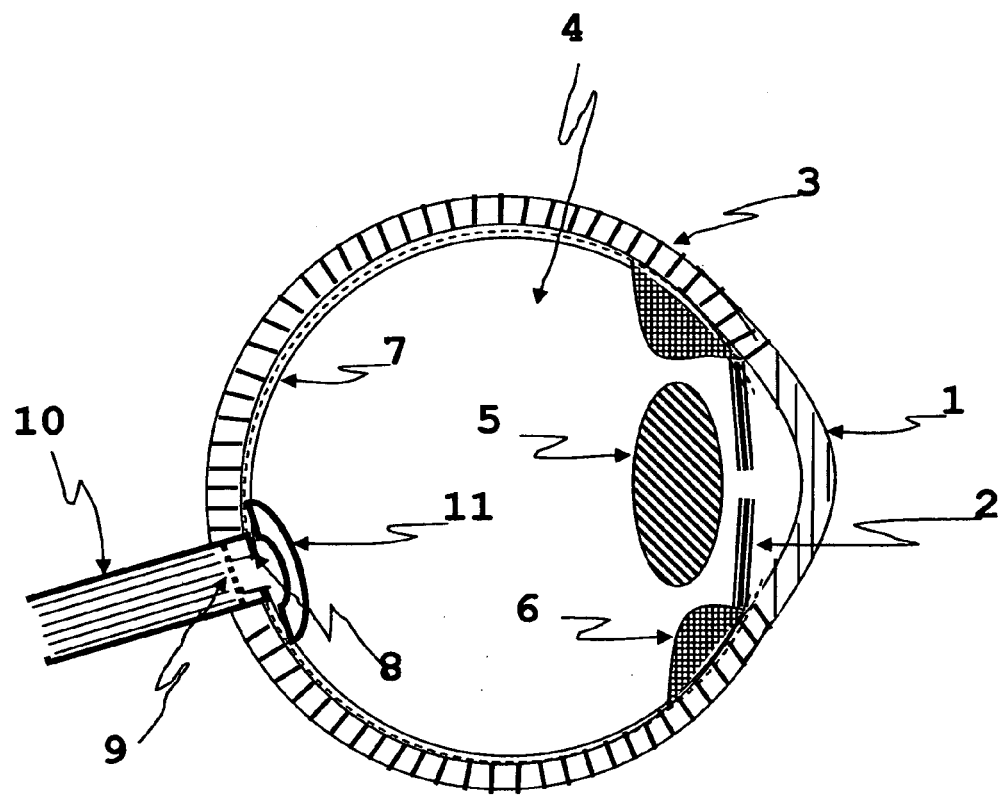
FIG. 1 illustrates a cross-sectional schematic view of a human eye of an embodiment using the optic nerve head shield in accordance with the present invention.

FIG. 1 illustrates a schematic diagram of one such embodiment, which employs the optic nerve head shield, 11, which was surgically implanted through the sclera, 3, posterior to the cornea, 1, iris, 2, crystalline lens, 5, and ciliary body, 6, into the vitreous cavity, 4, so that the optic nerve head shield, 11, is proximate and concentric to the optic nerve head, 8, and fixated to the retina, 7, by suction between the optic nerve head shield, 11, and the retinal surface, 7, to maintain fixation of the device over the optic nerve head, 8, and anterior to the cribiform plate, 9, and optic nerve, 10.

Figure 2:
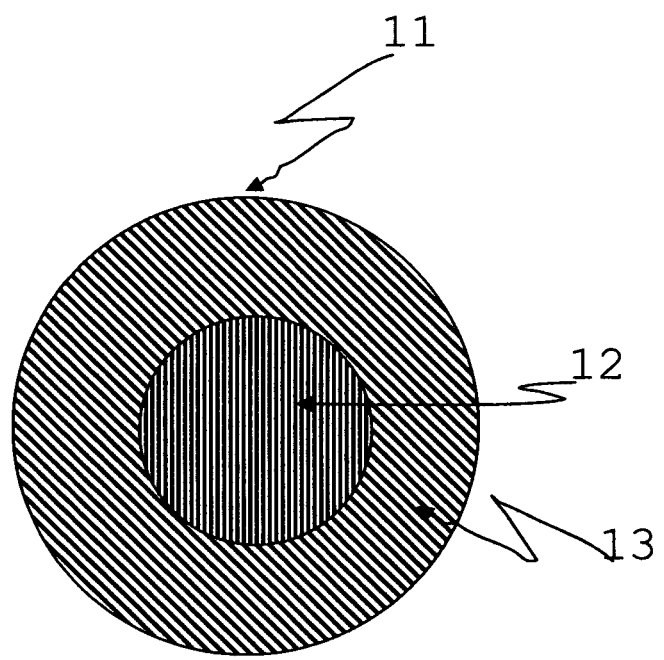
FIG. 2 is a schematic top view of an embodiment of the optic nerve head shield.

FIG. 2 is a schematic top view of an embodiment of the optic nerve head shield, 11, illustrating the stiffer central part, 12, and the more flexible concentric peripheral part 13.

Figure 3:
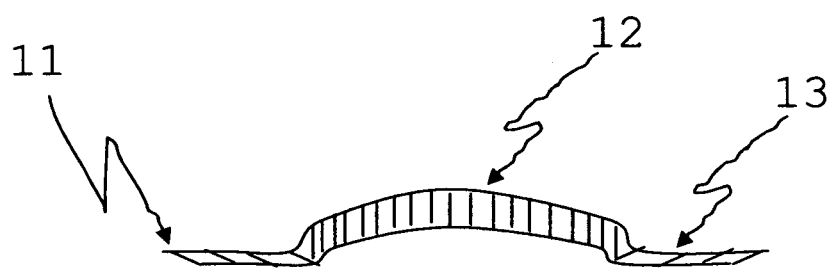
FIG. 3 is a schematic side view of an embodiment of the optic nerve head shield.

FIG. 3 is a schematic side view of an embodiment of the optic nerve head shield, 11, illustrating the stiffer central part, 12, and the more flexible concentric peripheral part 13.

Figure 4:
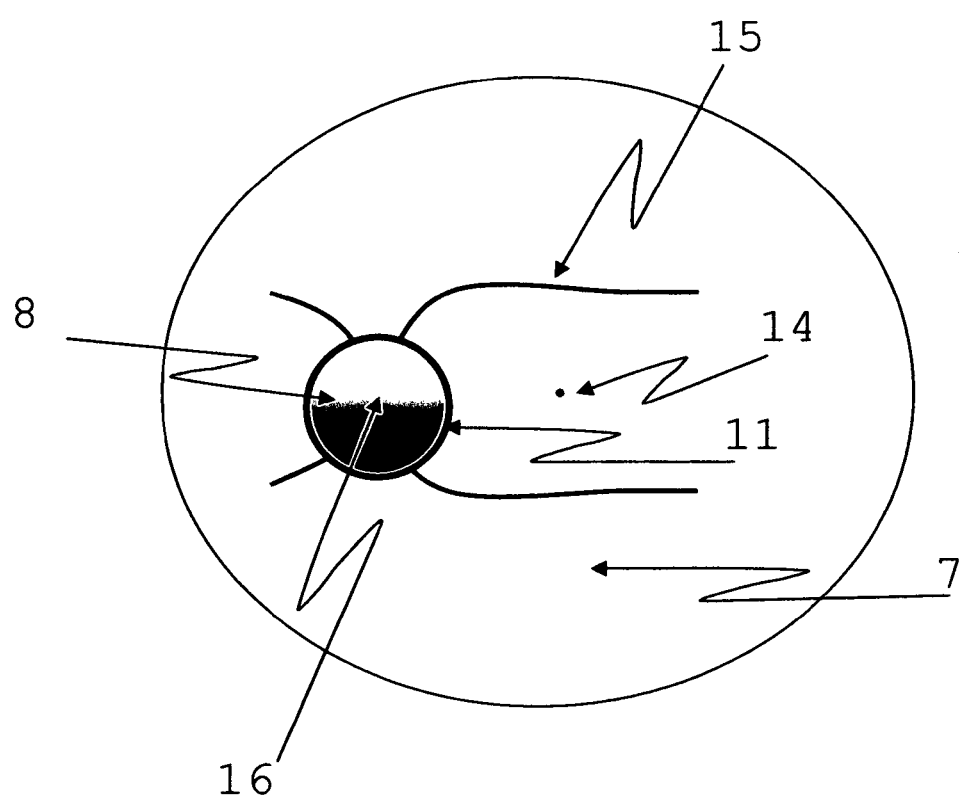
FIG. 4 illustrates the fundus of the human eye of an embodiment using the optic nerve head shield in accordance with the present invention.

FIG. 4 illustrates the fundus of the human eye of an embodiment with the optic nerve head shield, 11, nasal to the fovea, 14, held in place by suction to the retina, 7, and concentric to the optic nerve head, 8, so that the optic nerve head shield, 11, covers the optic nerve head, 8, its cup, 16, and the retinal vessels, 15, as they exit from the optic nerve head, 8.

Figure 5:
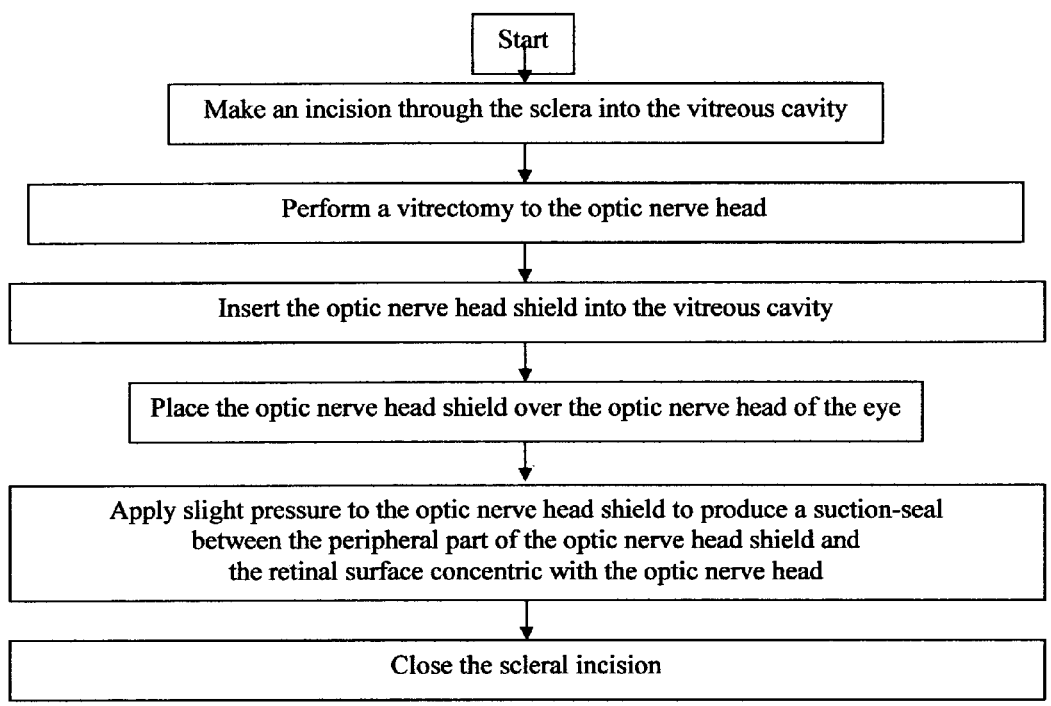
FIG. 5 is a flow diagram of an embodiment using an optic nerve head shield in accordance with the present invention.

FIG. 5 is a flow diagram of an embodiment using an optic nerve head shield in accordance with the present invention. An incision is made in the sclera, a vitrectomy to the optic nerve head is performed, the optic nerve head shield is placed over the optic nerve head, slight pressure is applied to the optic nerve head shield to produce a suction-seal between the peripheral part of the optic nerve head shield and the retina that is concentric to the optic nerve head, the sclera is closed.

What is claimed is:

1. An intraocular device for preventing glaucomatous optic neuropathy, the device comprising:
    an optic nerve head shield configured to be placed within an eye of a human or animal; and
    the optic nerve head shield is configured to be disposed directly over and without penetrating an optic nerve head of the eye and is configured to form a suction pressure seal over the optic nerve head,
    wherein the optic nerve head shield is a circular cover comprising a central stiffer part and a more flexible concentric peripheral part,
    wherein the flexible peripheral part is contoured to fit over retinal vessels of the eye and to form a pressure seal with the retinal vessels as the retinal vessels exit the optic nerve head,
    wherein the optic nerve head shield is concentric with the optic nerve head and is held in place by suction between the device and a retina of the eye, and
    wherein the optic nerve head shield is configured to decrease the pressure differential across the cribiform plate of the eye preventing bowing of the cribiform plate and glaucomatous optic neuropathy.

2. The device as claimed in claim 1, wherein the optic nerve head shield is made of a biocompatible material.

3. The device as claimed in claim 1, wherein a peripheral edge of the optic nerve head shield is serrated for fixation of the device to a retina of the eye and/or to a rim of the optic nerve head.

4. The device as claimed in claim 1, wherein there are holes provided in a peripheral edge of the optic nerve head shield for accommodating retinal tacks and/or hooks to fixate the device to a retina of the eye and/or to a rim of the optic nerve head.

5. The device as claimed in claim 1, wherein the optic nerve head shield is convex-concave.

6. The device as claimed in claim 1, wherein the optic nerve head shield is planar.

7. The device as claimed in claim 1, wherein the optic nerve shield comprises two or more biocompatible materials.

8. The device as claimed in claim 1, wherein the optic nerve head shield comprises two biocompatible materials, including the stiffer central part and the flexible peripheral part respectively made of the two biocompatible materials.

* * * * *